Figure 1:
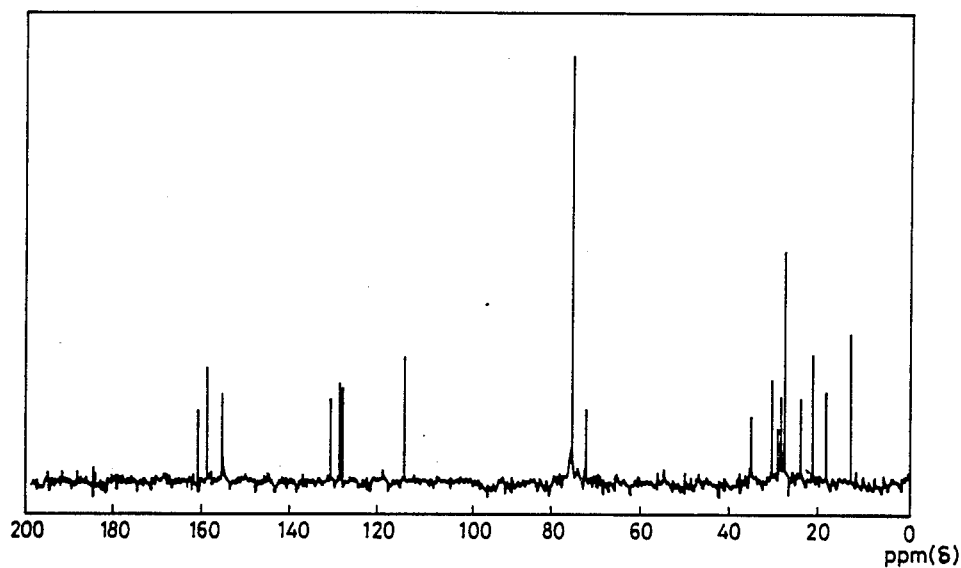

United States Patent [19]

Kano

[11] Patent Number: 4,851,529

[45] Date of Patent: Jul. 25, 1989

[54] PYRIMIDINE COMPOUND

[75] Inventor: Mitsuru Kano, Furukawa, Japan

[73] Assignee: Alps Electric Co., Ltd., Japan

[21] Appl. No.: 180,298

[22] Filed: Apr. 12, 1988

[30] Foreign Application Priority Data

Jul. 21, 1987 [JP] Japan ................... 62-181421

[51] Int. Cl.$^4$ .......................... C07D 239/26
[52] U.S. Cl. ................................. 544/335
[58] Field of Search ......................... 544/335

[56] References Cited

PUBLICATIONS

Petrzila et al., Chemical Abstracts, vol. 105, Entry 235973v, (1986).
Ine et al., Chemical Abstracts, vol. 198, Entry 177868p, (1988).

*Primary Examiner*—John M. Ford
*Attorney, Agent, or Firm*—Guy W. Shoup; Paul J. Winters

[57] ABSTRACT

A pyrimidine compound represented by the general formula:

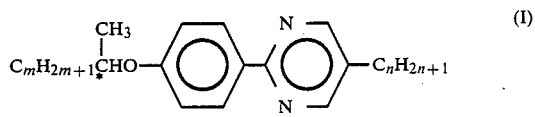

(I)

where m and n represent respectively integers as: $4 \leq m \leq 8$ and $6 \leq n \leq 14$. Pyrimidine compound according to the present invention shows Sc* phase at a low temperature below the room temperature and has extremely large spontaneous polarization as compared with the conventional compound, the performance of the liquid crystal element can be improved significantly.

8 Claims, 1 Drawing Sheet

WAVE NUMBER (cm⁻¹)

PYRIMIDINE COMPOUND

BACKGROUND OF THE INVENTION

1. Field of the Invention

The present invention concerns a pyrimidine compound that can be utilized as ferroelectric liquid crystals.

2. Description of the Prior Art

Among liquid crystal compounds inducing twisted arrangements, i.e., ferroelectric liquid crystal compounds, there have been not a many compounds having the chiral smectic C phase at a temperature lower than the room temperature (hereinafter simply referred to as the Sc* phase).

Among them, pyrimidine liquid crystal compounds, for example, the compound 1 represented by the following formula (1) disclosed in Japanese Patent Laid Open No. Sho 61-22072 shows a relatively low Sc* phase-forming temperature.

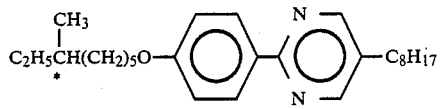

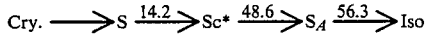

However, the spontaneous polarization (Ps) of the compound is as small as less than 1 nC (cm$^2$) at the greatest and, accordingly, it has a problem that the response under the room temperature is as slow as more than 1 ms.

In order to improve such a problem, the compound as shown by the formula (2) has been considered (refer to the pre-text for the 11th Liquid Crystals Meeting, 164 (S 60)).

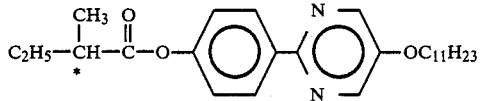

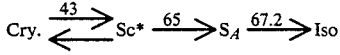

The compound 2 shows a great spontaneous polarization value of greater than 10 nC/cm$^2$. However, the compound 2 also has a problem that the Sc* phase does not appear at a low temperature lower than the room temperature.

The present invention has been made in view of the foregoing situation and it is an object thereof to provide a novel liquid crystal compound the Sc* phase of which is present near or less than the room temperature and having a large spontaneous polarization.

The pyrimidine compound according to the present invention is represented by the following general formula (1).

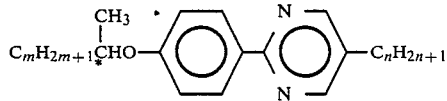

where m, n represent respectively integers as: $4 \leq m \leq 8$, $6 \leq n \leq 14$.

The compound represented by the general formula (1) has the Sc* phase at a low temperature below the room temperature and also has a large spontaneous polarization.

BRIEF DESCRIPTION OF THE ACCOMPANYING DRAWINGS

Figure 2:
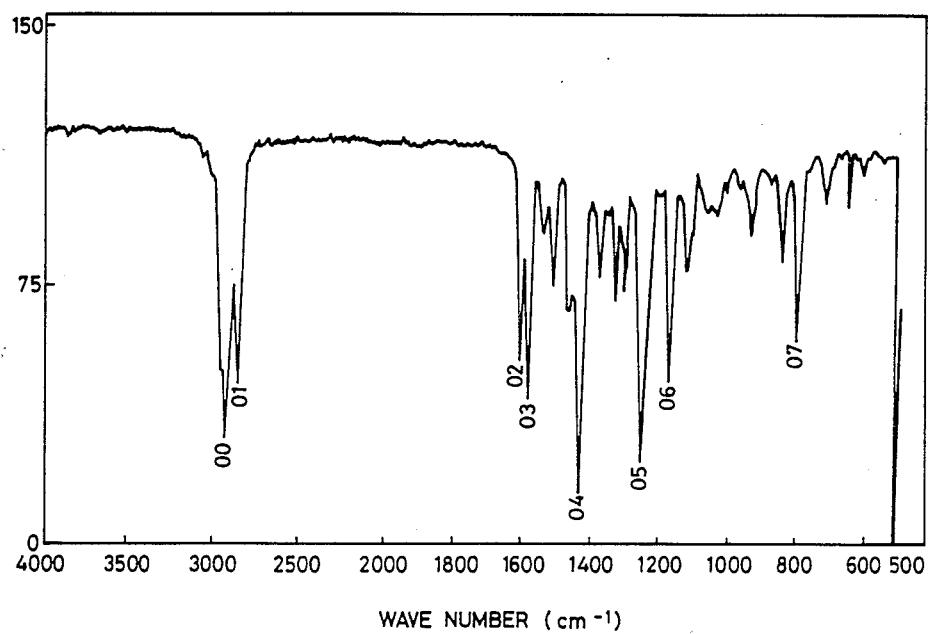

These and other objects, as well as advantageous features of the present invention will become apparent by leading the descriptions of the following preferred examples according to the present invention in conjunction with the appended drawings, wherein:

FIG. 1 is a chart illustrating the result of $^{13}$C-NMR analysis for the compound 3 in Example 1; and FIG. 2 is a chart illustrating IR absorption Spectrum for the compound 3 in Example 1.

EXAMPLE

The ester compound according to the present invention will be described more specifically referring to examples.

Examples 1, 2

Pyrimidine compounds 3, 4 of the present invention represented by the formulae (3) and (4) were synthesized and their transition temperatures were examined (symbols (S) and (R) appended to the following formulae show that the relevant portions of the side chains were synthesized from starting alcohols of absolute arrangement (S) or (R).

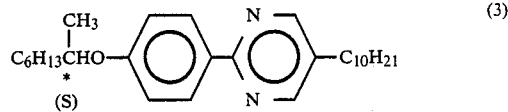

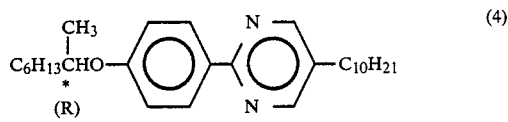

The compounds 3 and 4 were synthesized as described below.

At first, alcohol tosyl ester was synthesized by reacting S-2-octanol (Example 1) or R-2-octanol (Example 2) and tosyl chloride. Then, the tosyl ester and a commercially available intermediate product C shown by the formula (C) were added into ethanol where sodium hydroxide was present. They were reacted for about 24 hours while stirring sufficiently under a reflux temperature.

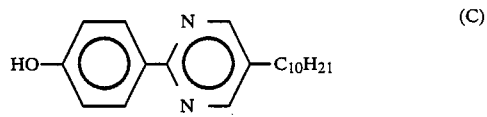

Then, the resultant reaction solution was cooled to the room temperature and, after distilling off ethanol, extracted with toluene. Then, the extracted liquid was washed with usual procedures and then toluene was distilled off. The residue was purified by developing on silica gel column chromatography by using a chloroform/hexane solution (1/9 ratio) as an elute to obtain the compounds 3, 4 of the formulae (3) and (4).

The phase transition temperature and the spontaneous polarization of the ester compounds 3, 4 prepared by the above-mentioned procedures were examined, to obtain the results as shown in Table 1.

TABLE 1

| | Phase transition (C) | Spontaneous polarization |
|---|---|---|
| Example 1 | Cry. −12 → Iso; −30; Sc* ←−15 S_A; −13.6 | 5 5 nC/cm² |
| Example 2 | " | " |

Note: The value for the spontaneous polarization was shown by the maximum value.

From the result in Table 1, it can be seen that both of the pyrimidine compounds 3, 4 in Examples 1, 2 have extremely greater spontaneous polarization as compared with the conventional pyrimidine compound 1 and they have the Sc* phase near the room temperature.

Subsequently, the compound 3 of Example 1 was examined by $^{13}$C-NMR and IR absorption method. The results are shown in FIG. 1 and FIG. 2. In the $^{13}$C-NMR chart shown in FIG. 1, the peak at 76 ppm is a peak given from chloroform used as a solvent. It can be estimated the presence of an alkoxy group from the peak at 73 ppm present on the side of the higher magnetic field from the above-mentioned peak, while the presence of seven carbons on the side of the alkoxy group from seven peaks present on the side of the lower magnetic field. In FIG. 2, the wave number for each of the peaks is as shown in Table 2.

From the results, it could be confirmed that the compound 3 has the structure of the formula 3 as described above.

TABLE 2

| Peak number | Wave number |
|---|---|
| 00 | 2940 |
| 01 | 2860 |
| 02 | 1610 |
| 03 | 1590 |
| 04 | 1440 |
| 05 | 1260 |
| 06 | 1175 |
| 07 | 800 |

Examples 3, 4

Compounds 5, 6 of the following formulae (5), (6) were synthesized by using the intermediate product D represented by the following formula (D) instead of the intermediate product C used in Examples 1, 2 and by the same procedures as those in Example 1.

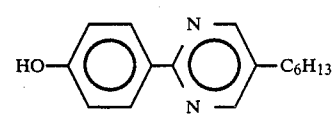
(D)

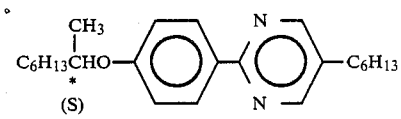
(5)

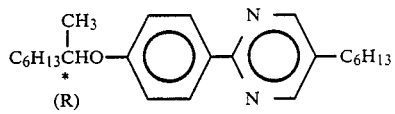
(6)

When the phase transition temperature and the spontaneous polarization of these compounds 5, 6 were examined, substantially the same results as those for the compounds 3, 4 of Examples 1, 2 were obtained.

Examples 5, 6

The same procedures as those in Example 1 were carried out by using S-2-hexanol (Example 5) and S-2-decanol (Example 6) in stead of S-2-octanol, to obtain a compound 7 represented by the following formula:

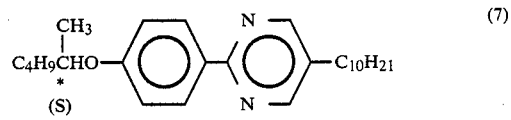
(7)

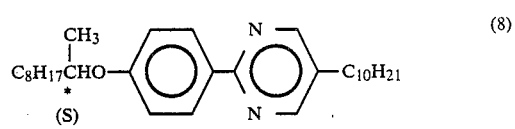
(8)

When the phase transition temperature and the spontaneous polarization of the compounds 7, 8 were examined, substantially the same result as those of the compounds of Example 1 were obtained.

Example 7

The same procedures as those in Example 1 were carried out by using an intermediate E represented by the following formula (E) instead of the intermediate product C used in Example 1, to synthesize a compound 9 represented by the following formula (9):

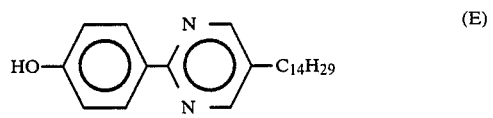
(E)

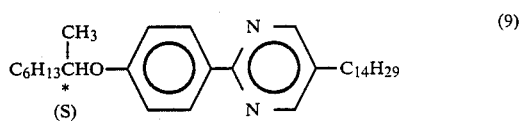
(9)

When the phase transition temperature and the spontaneous polarization of the compound 9 were examined, substantially the same results as those for the compound 3 of Example 1 were obtained.

As has been described above, since the pyrimidine compound according to the present invention has the Sc* phase at a low temperature below the room temperature and the spontaneous polarization extremely greater as compared with that of the conventional compound, the performance of the liquid crystal element can be improved remarkably.

What is claimed is:

1. A pyrimidine compound represented by the general formula:

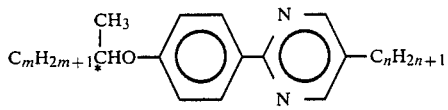 (I)

where m and n represent respectively integers as:
$4 \leq m \leq 8$, $6 \leq n \leq 14$.

2. A pyrimidine compound as defined in claim 1, having the formula:

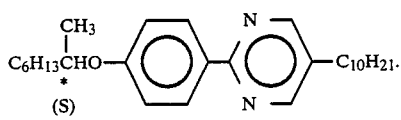 (3)

3. A pyrimidine compound as defined in claim 1, having the formula:

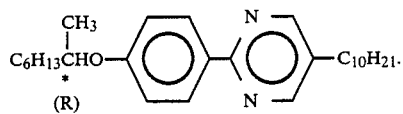 (4)

4. A pyrimidine compound as defined in claim 1, having the formula:

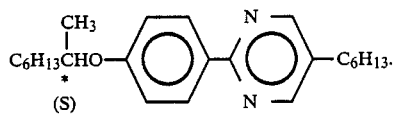 (5)

5. A pyrimidine compound as defined in claim 1, having the formula:

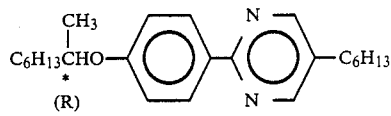 (6)

6. A pyrimidine compound as defined in claim 1, having the formula:

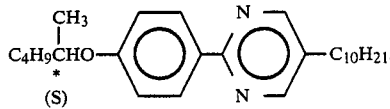 (7)

7. A pyrimidine compound as defined in claim 1, having the formula:

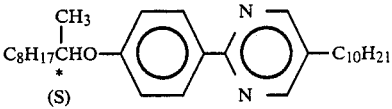 (8)

8. A pyrimidine compound as defined in claim 1, having the formula:

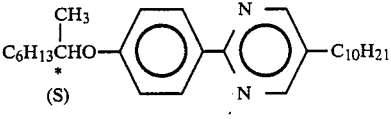 (9)

* * * * *